(12) United States Patent
Krutz et al.

(10) Patent No.: US 10,359,387 B2
(45) Date of Patent: Jul. 23, 2019

(54) HYDRAULIC HOSES WITH LIFE-SENSING CAPABILITY AND METHODS THEREFOR

(71) Applicant: Purdue Research Foundation, West Lafayette, IN (US)

(72) Inventors: Gary W. Krutz, West Lafayette, IN (US); Brittany Newell, Delphi, IN (US); Grant Knies, Celestine, IN (US)

(73) Assignee: Purdue Research Foundation, West Lafayette, IN (US)

( * ) Notice: Subject to any disclaimer, the term of this patent is extended or adjusted under 35 U.S.C. 154(b) by 0 days.

(21) Appl. No.: 15/549,700

(22) PCT Filed: Mar. 14, 2016

(86) PCT No.: PCT/US2016/022333
§ 371 (c)(1),
(2) Date: Aug. 9, 2017

(87) PCT Pub. No.: WO2016/149197
PCT Pub. Date: Sep. 22, 2016

(65) Prior Publication Data
US 2018/0074005 A1     Mar. 15, 2018

Related U.S. Application Data

(60) Provisional application No. 62/132,945, filed on Mar. 13, 2015.

(51) Int. Cl.
*F16L 55/00*     (2006.01)
*G01N 27/24*     (2006.01)
(Continued)

(52) U.S. Cl.
CPC .............. *G01N 27/24* (2013.01); *B29C 70/88* (2013.01); *G01N 27/20* (2013.01); *F16L 55/07* (2013.01)

(58) Field of Classification Search
CPC ..... F16L 11/127; F16L 25/01; F16L 2201/30; G01N 27/02
(Continued)

(56) References Cited

U.S. PATENT DOCUMENTS 2,320,367 A * 6/1943 Ward ..................... F16L 11/127
                                                     15/314
5,381,834 A * 1/1995 King ..................... F16L 11/085
                                                    138/103
(Continued)

FOREIGN PATENT DOCUMENTS

EP          0185650        9/1988

OTHER PUBLICATIONS

International Search Report, PCT/US2016/022333 dated Jun. 10, 2016.

*Primary Examiner* — Patrick F Brinson
(74) *Attorney, Agent, or Firm* — Hartman Global IP Law; Gary M. Hartman; Domenica N. S. Hartman

(57) ABSTRACT

A system and methods for predicting structural failure of at least a portion of a wall of a fluid containment vessel. The wall has an innermost layer for contact with a fluid contained by the vessel and an outermost layer parallel with the innermost layer. The system includes strain-sensing means within a portion of the wall and surrounded by the at least one reinforcement layer including at least one conductor parallel to the innermost layer of the wall. Changes are sensed in an electrical property associated with the at least one conductor resulting from distortion of the wall of the vessel causing distortion of the at least one conductor.

14 Claims, 5 Drawing Sheets

(51) Int. Cl.
  *B29C 70/88* (2006.01)
  *G01N 27/20* (2006.01)
  *F16L 55/07* (2006.01)

(58) Field of Classification Search
  USPC .... 138/104, 123–127, 36; 73/49.5, 40, 49.1, 73/49.2
  See application file for complete search history.

(56) References Cited

U.S. PATENT DOCUMENTS

| | | | |
|---|---|---|---|
| 5,431,191 A * | 7/1995 | Neuhauser | F16L 11/127 138/103 |
| 5,551,484 A | 9/1996 | Charboneau | |
| 5,969,618 A * | 10/1999 | Redmond | G01M 3/18 174/11 R |
| 6,361,299 B1 | 3/2002 | Peter et al. | |
| 6,386,237 B1 * | 5/2002 | Chevalier | F16L 11/12 116/208 |
| 6,498,991 B1 * | 12/2002 | Phelan | G01M 3/18 138/104 |
| 7,555,936 B2 | 7/2009 | Deckard | |
| 7,861,746 B2 * | 1/2011 | Zimmer | F16L 11/127 138/125 |
| 8,997,792 B2 * | 4/2015 | Betsinger | F16L 57/06 138/104 |
| 2014/0000742 A1 * | 1/2014 | Betsinger | F16L 57/06 138/36 |

* cited by examiner

HYDRAULIC HOSES WITH LIFE-SENSING CAPABILITY AND METHODS THEREFOR

CROSS REFERENCE TO RELATED APPLICATIONS

This application claims the benefit of International Application No. PCT/US2016/022333, filed Mar. 4, 2016, which claims the benefit of U.S. Provisional Application No. 62/132,945, filed Mar. 13, 2015.

BACKGROUND OF THE INVENTION

The present invention generally relates to vessels that contain static or flowing fluids, including conduits such as hydraulic hoses of the types used in mobile machinery, automotive, aerospace, manufacturing, and process equipment. The invention particularly relates to hydraulic hoses equipped with means for sensing the life of the hose in terms of wear, fatigue, and/or other structural breakdown of its components, and means for electrically monitoring the hose to predict a structural failure.

Interest exists in developing methods for consistently predicting the failure of vessels containing fluids, including but not limited to hoses, thereby enabling replacement or repair of the vessel before failure from normal wear and/or quality issues that could result in equipment down time and safety concerns.

A hose 20 of a type known in the art is represented in FIG. 1. The hose 20 is representative of various types of hoses that may be used to contain a flowing or static fluid under high pressure conditions. A particular example is a hydraulic hose that contains a hydraulic fluid whose pressure fluctuates. The hose 20 is represented as having an inner tube 22 that contacts a fluid flowing through the hose 20, four reinforcement layers 24 that strengthen the hose 20, intermediate layers 28 between the reinforcement layers 24, and an outer cover 26 that protects the hose 20 and its interior components. Because the inner tube 22 directly contacts the fluid, the material from which the inner tube 22 is formed must be chemically compatible with the fluid contained by the hose 20. The reinforcement layers 24 promote the strength of the hose 20. Any number of reinforcement layers 24 may be present in the hose 20, and reinforcement layers 24 have been constructed from a variety of materials in a variety of configurations, commonly a spiral metal configuration. If multiple reinforcement layers 24 are used, the intermediate layers 28 (for example, formed of a polymer material) can serve as separation layers between the reinforcement layer 24 to reduce abrasion and wear therebetween.

It is conventional to equip the ends of the hose 20 with fittings to permit connection of the hose 20 to other hoses or equipment in a system containing the hose 20. Typical fittings include a nipple that is forced into the opening of the inner tube 22, and an outer collar or socket that is crimped onto the exterior of the hose 20 and onto a portion of the nipple that protrudes from the hose 20. The socket is typically equipped with barbs that are forced through the outer cover 26 and into an outermost reinforcement layer 24 during crimping to secure the fitting on the hose 20. Close tolerances are required to achieve a fluid-tight seal between the hose 20 and the fitting, necessitating a wide variety of fittings in various sizes for use on hoses of different sizes.

Hydraulic hoses of the type represented in FIG. 1 may fail by a variety of mechanisms, including abrasion, loading, fatigue, and environmental factors relating to the hose as well as its fittings and the fluid therein. Because hydraulic hoses are often subject to cyclic loading as a result of pressure changes during startup, shutdown, and normal operation of a hydraulic system, fatigue is an important factor in the life of hydraulic hoses and their fittings. The fatigue rate can increase markedly as a result of damage to the inner tube 22, reinforcement layers 24, and outer cover 26 of the hose 20, as well as damage to the hose fittings.

An example of a life-sensing hose which uses changes in resistance and/or capacitance to predict component failures was disclosed in U.S. Pat. No. 7,555,936 to Deckard. A wide range of hydraulic hoses is encompassed by Deckard, including hoses suitable for medium pressure applications. The terms "medium pressure hydraulic hose" and "high pressure hydraulic hose" will be used herein as defined by the Society of Automotive Engineers (SAE) Standard J517, which defines specifications such as maximum operating pressures for various types of hydraulic hoses. The structure for low, medium, and high pressure hoses are significantly different, limiting the applicability of this type of technology from directly translating between applications. Low pressure hoses are conventionally composed of fiber-based materials such as Kevlar and polymers, high pressure hoses are conventionally composed of many layers of polymers and spiral wire, and medium pressure hoses generally utilize biaxial braided wire as a primary means of strength. The braided wire may be surrounded by rubber components. For this type of hoses, an additional concentric layer of wire may be added separated by the rubber from the first layer of braided wire, thereby creating a cylindrical parallel plate capacitor. As the hose fatigues, individual wires may begin to break within the circuit and pop out into the rubber layer causing a short or change in the overall capacitance that can be utilized to predict early failure. However in low and high pressure hoses, braided wire is not typically used.

It would be desirable if methods and non-braided wire-based hoses were available that made it possible to not only sense an imminent fatigue failure of a hydraulic hose, but were also capable of predicting when a structural failure of the hose may occur so that the hose can be safely used for its full life span and then replaced before failure, thereby reducing the likelihood that damage occurs to a fluid system containing the hose or the apparatus employing the hose as a result of a catastrophic failure.

BRIEF DESCRIPTION OF THE INVENTION

The present invention provides systems and methods suitable for predicting a structural failure of a vessel containing a fluid.

According to one aspect of the invention, a system is provided for predicting structural failure of at least a portion of a wall of a fluid containment vessel that has an innermost layer for contact with a fluid contained by the vessel, an outermost layer parallel with the innermost layer, and at least one reinforcement layer between the innermost and outermost layers and parallel to the innermost layer. The system includes strain-sensing means within the portion of the wall and surrounded by the at least one reinforcement layer. The strain-sensing means comprises at least one conductor parallel to the outermost layer of the wall and means for sensing changes in an electrical property associated with the at least one conductor resulting from distortion of the wall of the vessel that causes distortion of the at least one conductor, wherein the electrical property is chosen from the group consisting of electrical capacitance, electrical resistance, electrical inductance, electrical reactance, and combinations thereof.

According to another aspect of the invention, a method of predicting structural failure of at least a portion of a wall of a vessel containing a fluid includes forming the wall to have an innermost layer for contact with a fluid contained by the vessel, an outermost layer parallel with the innermost layer, at least one reinforcement layer between the innermost and outermost layers and parallel to the innermost layer, and strain-sensing means within the portion of the wall and surrounded by the at least one reinforcement layer. The strain-sensing means comprises at least one conductor parallel to the outermost layer of the wall, and senses changes in an electrical property associated with the at least one conductor resulting from distortion of the wall of the vessel that causes distortion of the at least one conductor, wherein the electrical property is chosen from the group consisting of electrical capacitance, electrical resistance, electrical inductance, electrical reactance, and combinations thereof.

Technical effects of the system and method described above preferably include the capability of electrically monitoring a fluid containment vessel as described above, and particularly monitoring electrical capacitance with respect to a preestablished acceptable range, to enable accurate predictions of wall failures as a result of electrical changes being generally nominal until an abrupt or sufficiently large gradual electrical change occurs that sufficiently precedes a failure. In this manner, the wall can be repaired or the vessel replaced before any harm occurs to a system or apparatus in which the vessel is used.

Other aspects and advantages of this invention will be better appreciated from the following detailed description.

DETAILED DESCRIPTION OF THE INVENTION

The present invention provides systems and methods for predicting structural failures in walls of fluid containment vessels, for example, a hydraulic hose or other type of pressurized conduit of types used in mobile machinery, automotive, aerospace, manufacturing, and process equipment. More specifically, the present invention provides methods suitable for performing life-sensing in non-braided wire-based hydraulic hoses, particularly high pressure hoses comprising multiple layers rubber and spiral wire, wherein a warning signal indicating failure of individual layers, for example an inner layer, of the hose can be provided. The invention involves creating an electrical circuit within a wall of a fluid containment vessel, such as a hydraulic hose, and sensing changes in an electrical property responsive to distortion of the wall, which can evidence wear, fatigue, and/or other structural breakdown of the vessel. According to preferred embodiments of the invention, the electrical property of interest is electrical capacitance, electrical resistance, electrical inductance, electrical reactance, or a combination thereof, and conductive, dielectric, and/or resistive layers are formed as necessary to create an electrical capacitor and/or resistor within at least one portion of the wall of the vessel, by which changes in capacitance, inductance, reactance, and/or resistance are sensed.

Figure 1:
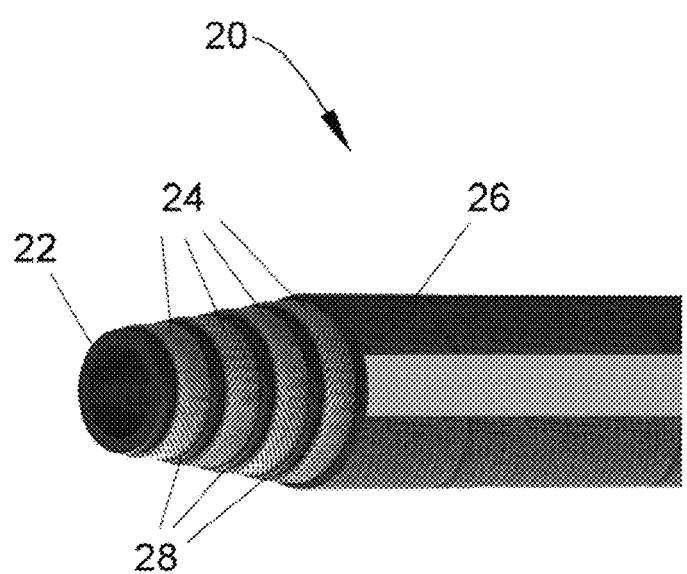
FIG. 1 represents a hydraulic hose of a type known in the art, with layers of the hose exposed to show the hose construction.

Hoses of types commonly used for high pressure applications, such as the hose 20 represented in FIG. 1, may include a structure composed of layered dielectric and conductive materials including multiple metal layers and, for example, materials designed to withstand a high pressure environment. According to one aspect of the invention, a hose may incorporate additional layers into interior layers of the hose to form an electrical circuit to detect hose deterioration from interior failures which are the most difficult to detect and very common. Alternatively, the hose may incorporate additional layers to form multiple capacitance circuits throughout the thickness of the wall of the hose to preferably sense changes in an electrical property at various levels within the hose, with the intent of providing enhanced sensitivity. Multiple capacitance circuits can be created by layering conductive polymer, dielectric polymer, and/or spiral metal layers within the wall of a hose.

Figure 2:
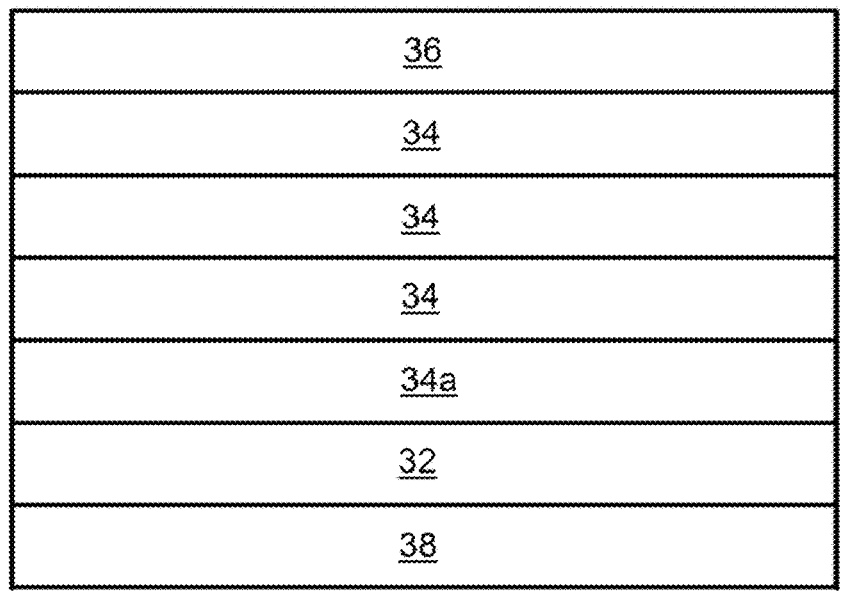
FIGS. 2 and 3 schematically represent layers of hoses in accordance with certain nonlimiting aspects of the invention.
Figure 3:
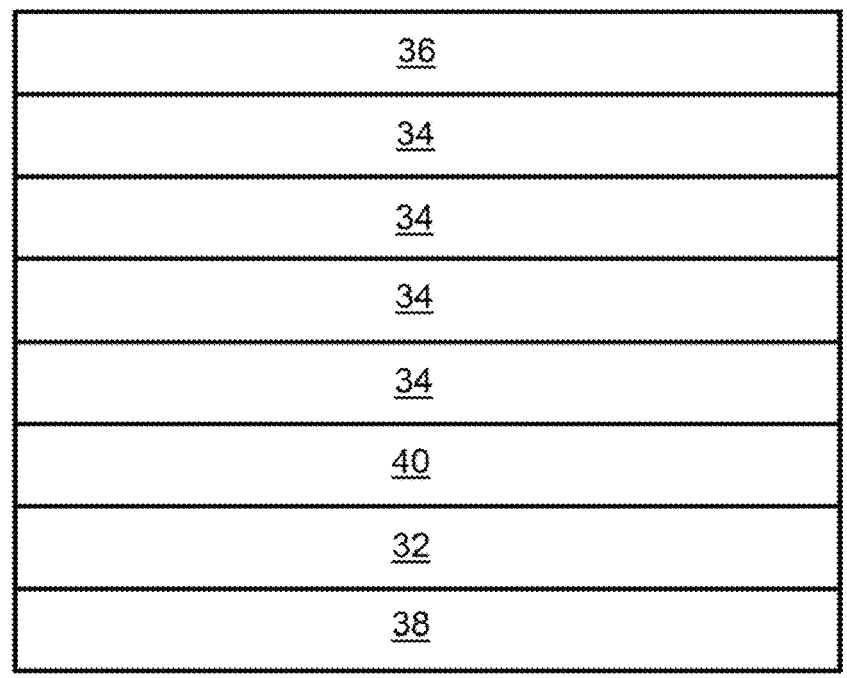

FIGS. 2 and 3 represent nonlimiting embodiments of high pressure hoses comprising a single capacitance circuit. Although the capacitance circuits are represented as being located at or near innermost layers of the hoses, it is within the scope of the invention that such circuits may be located at any suitable location or multiple locations across a thickness of the hoses. For convenience, consistent reference numbers are used throughout the drawings to identify the same or functionally equivalent elements. It should be noted that the drawings are drawn for purposes of clarity when viewed in combination with the following description, and therefore are not necessarily to scale.

FIG. 2 represents a first nonlimiting embodiment of a hose having a first conductive layer 38, a first dielectric layer 32, four spiral metal reinforcement layers 34 (an innermost of the layers 34 referred to as a first spiral metal reinforcement layer 34a), and an outermost cover layer 36. In addition, intermediate polymer layers (not shown) may be located between one or more adjacent pairs of the reinforcement layers 34 as is common in high pressure hoses. In this nonlimiting embodiment, the first conductive layer 38, the first dielectric layer 32, and the reinforcement layer 34a form a capacitance bridge or capacitive coupling. As such, capacitance may be measured between the first conductive layer 38 and the reinforcement layer 34a.

FIG. 3 represents a second nonlimiting embodiment of a hose having a first conductive layer 38, second dielectric layer 32, four spiral metal reinforcement layers 34, and outermost cover layer 36 similar to FIG. 2, and in addition a second conductive layer 40 between the second dielectric layer 32 and the innermost reinforcement layer 34. As before, intermediate polymer layers (not shown) may be located between the reinforcement layers 34 as is common in high pressure hoses. In this nonlimiting embodiment, the first conductive layer 38, the first dielectric layer 32, and the second conductive layer 40 form a capacitance bridge or capacitive coupling. As such, capacitance may be measured between the first and second conductive layers 38 and 40.

Figure 4:
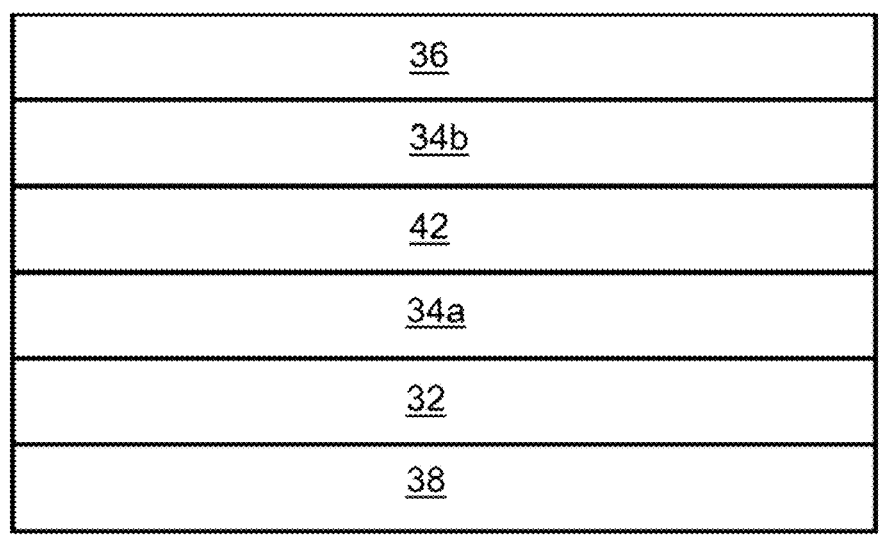
FIG. 4 schematically represents layers of a hose having multiple life sensing electrical circuits therein in accordance with certain nonlimiting aspects of the invention.

FIG. 4 represents a nonlimiting embodiment of a high pressure hose comprising multiple capacitance circuits. The hose includes a first conductive layer 38, second dielectric layer 32, spiral metal reinforcement layers 34 (which includes two designated as first and second spiral metal reinforcement layers 34a and 34b), and outermost cover layer 36 similar to FIG. 2, and in addition a second dielectric layer 42 between the first and second spiral metal reinforcement layers 34a and 34b. In this nonlimiting embodiment, the first conductive layer 38, the first dielectric layer 32, and the first reinforcement layer 34a form a first capacitance bridge or capacitive coupling, and the first reinforcement layer 34a, the second dielectric layer 42, and the second reinforcement layer 34b form a second capacitance bridge or capacitive coupling. As such, capacitance may be measured between the first conductive layer 38 and the first reinforcement layer 34a, as well as between the first reinforcement layer 34a and the second reinforcement layer 34b.

The first and second conductive layers 38 and 40 may be formed of any materials that are capable of surviving high pressure hydraulic hose applications and have a sufficiently higher dielectric constant than the dielectric layer 32. Nonlimiting examples of materials suitable for the first and second conductive layers 38 and 40 include polymer materials doped with conductive particles such as metals, carbon black, graphite, silver, and graphene to be conductive or low resistance (for example, a fluoroelastomer such as FKM (as defined in ASTM D1418) doped with conductive particles), or a conductive synthetic woven material such as a conductive ARACON® fiber material commercially availably from Micro-Coax, Inc. The first and second dielectric layers 32 and 42 may be formed of any material that is capable of surviving high pressure hydraulic hose applications. Nonlimiting examples include woven carbon fiber materials, Viton® (commercially available from DuPont Performance Elastomers LLC), FKM, EDPM (as defined by ASTM standard D-1418), nitrile butadiene rubber (NBR), and dielectric polymer materials of the types commonly used as inner layers of high pressure hydraulic hoses. It is within the scope of the invention that the first and second conductive layers 38 and 40 may be formed of different materials. Likewise, the first and second dielectric layers 32 and 42 may be formed of different materials.

Optionally, the first dielectric layer 32 may be formed of a material that reacts with the fluid within the hose in a manner that affects measured capacitance readings. For example, in the event that the first conductive layer 38 of FIG. 3 fails and allows oil to penetrate therethrough, the oil may react with the dielectric layer 32 and cause conductive properties of the dielectric layer 32 to change such that a change in capacitance can be detected. As a nonlimiting example, if the dielectric layer 32 comprises a silicone-based material, contact with oil may cause swelling of the dielectric layer 32, thereby forcing the first and second conductive layers 38 and 40 apart, resulting in a notable change in the capacitance of the capacitive bridge. In such embodiments, it is preferred that the second conductive layer 40 is capable of withstanding the operating pressure for a time period that is sufficient for a failure signal to be deployed and allow the system to be shut down for maintenance prior to failure of the hose.

Figure 5:
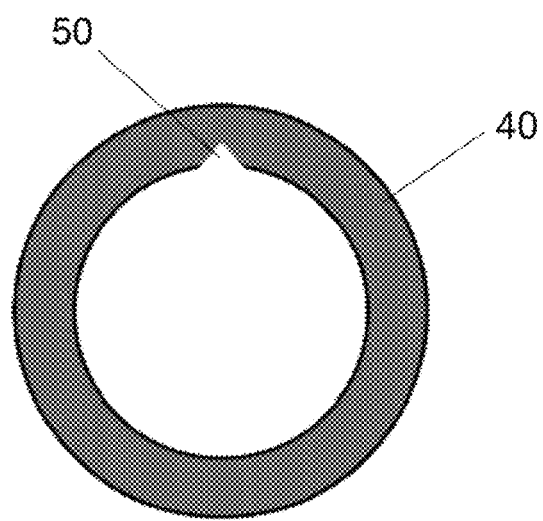
FIG. 5 represents a cross-sectional view of an isolated layer of a hose having a channel formed therein in accordance with a nonlimiting aspect of the invention.

In addition to sensing the capacitance of the electrical circuits, if one of the layers of the hose is formed of a sufficiently rigid material, one or more channels may be formed in an inner surface of the layer along a length of the hose. The channels allow for the oil to travel the length of the hose to a switch or other apparatus capable of detecting the oil and deploying a failure signal. FIG. 5 schematically represents a cross-sectional isolated view of the second conductive layer 40 modified in this manner to comprise a channel 50 formed in its internal surface in accordance with a nonlimiting embodiment of the invention.

Failure of a hydraulic hose of the types described herein may be predicted by monitoring the capacitance values of one or more capacitance bridges within the hose, with sufficient warning to enable the hose to be replaced before catastrophic failure occurs and prior to failure of the inner layers of the hose that might be detectable by other means. For this purpose, FIG. 6 represents a suitable system as including a monitor 60, a device 62 to calculate an acceptable range for the electrical capacitance of the capacitive coupling (e.g., based on an initial capacitance reading obtained from the hose), and a device 64 that generates a digital, visual, and/or audible signal that a structural failure of the hose is impending in view of the capacitive value deviating outside the acceptable range.

Electrical connection to the conductive layers of a hose may be through fittings specifically configured for this purpose. FIG. 6 represents a nonlimiting fitting 70 that is similar in construction to fittings used in the past with hydraulic hoses. The fitting 70 is represented in FIG. 6 as secured to a hose of the type represented in FIG. 2. The fitting 70 includes a nipple 72 that has been forced into the opening of the innermost layer of the hose, and a socket 74 that is crimped onto the exterior of the hose. The socket 74 is equipped with a crimp ring 76 that engages a channel on the nipple 72 to firmly secure the socket 74 to the nipple 72. The socket 74 is further equipped with barbs 78 that are forced through the outer cover 36 of the hose and into the outer conductive layer (reinforcement layer 34a) during crimping. In the embodiment of FIG. 6, the barbs 78 are defined by six concentric rings on the socket 74. If the inner conductive layer (first conductive layer 38) is the innermost layer of the hose, the nipple 72 will be in direct electrical contact therewith. However, if the inner conductive layer is not the innermost layer of the hose, the nipple 72 may include one or more barbs (not shown) that are sufficiently sharp to penetrate through the innermost layer and into the inner conductive layer during assembly and crimping of the hose and fitting 70. Finally, an insulator 80 is present between the ring 76 and channel of the socket 74 and nipple 72 so that these components of the fitting 70 are electrically insulated from each other. The insulator 80 may be formed of any material suitable for ensuring that the nipple 72 and socket 74 are only electrically connected through the one or more electrical circuits within the hose.

Figure 6:
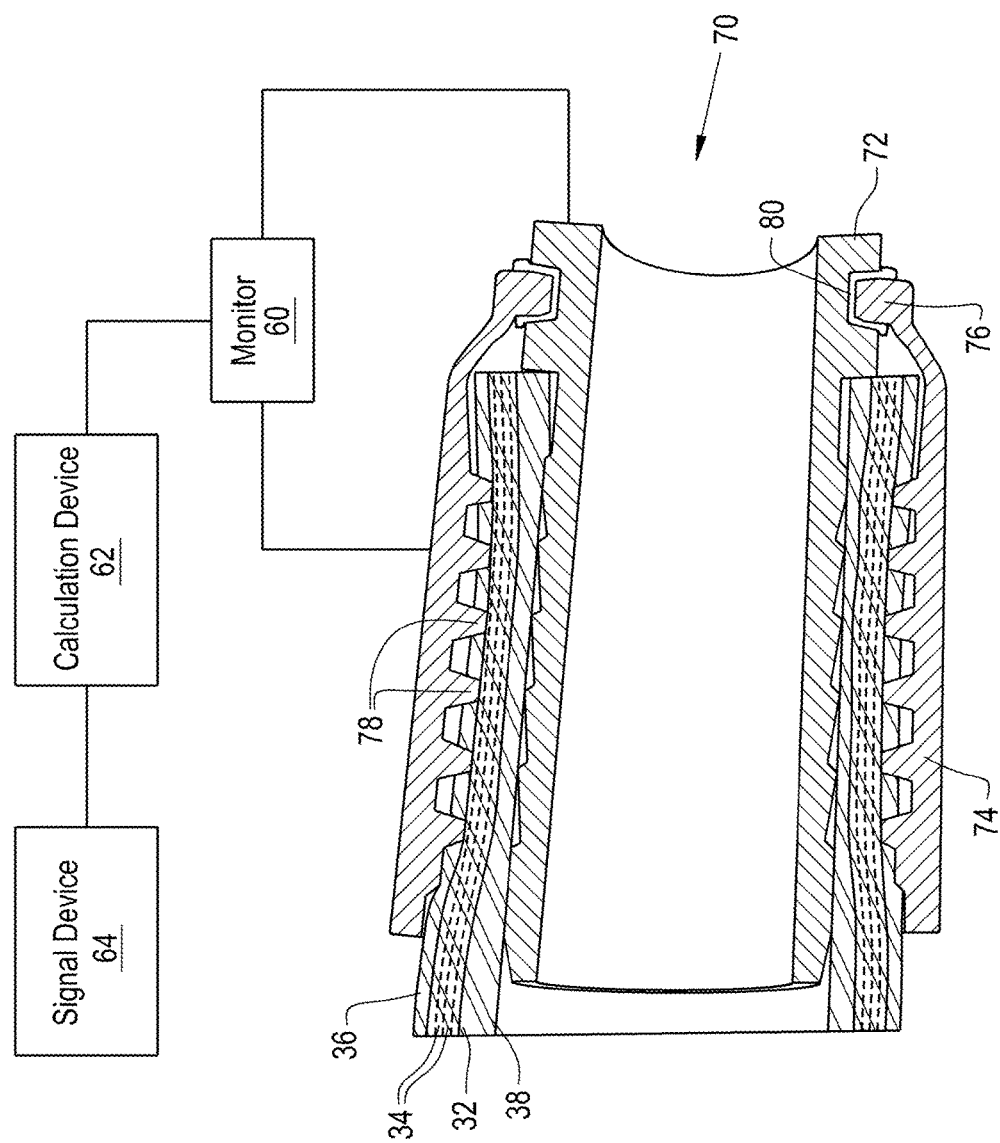
FIG. 6 shows a fitting of a type capable of use with hydraulic hose's of the type of FIG. 2 in accordance with a nonlimiting embodiment of this invention.

Electrical connection may be made to the conductive layer 38 and the reinforcement layer 34a of the hose of FIGS. 2 and 6 (or the first and second conductive layers 32 and 40 of the hose of FIG. 3) through the nipple 72 and socket 74, respectively, of the fitting 70. By providing and connecting the monitor 60 to the nipple 72 and socket 74 of the fitting 70, changes in the electrical capacitance of the capacitance bridge can be sensed. According to the invention, such changes are believed to occur as a result of material wear (fatigue, abrasion, compression, etc.), material puncture, or incompatible fluids which may break down or swell layers of a hose.

Capacitance of the electrical circuits can be calculated with the following equation 1.

$$C = \frac{2\pi K \varepsilon_0 L}{\ln\left(\frac{R_2}{R_1}\right)}. \qquad \text{Equation 1}$$

where C is capacitance in farads, K is the dielectric constant of the material (unitless), $\varepsilon_0$ is the permittivity of free space in farads/meter, L is the length of the capacitor coupling within the hose in meters, $R_1$ is the radius of the inner conductive layer in meters, and $R_2$ is the radius of the outer conductive layer in meters. According to the invention, for a unit length L of a hose, the radii of the inner and outer conductive layers ($R_1$ and $R_2$, respectively), the ratio $R_2/R_1$, and the dielectric constant of the insulating layer will change as the hydraulic hose fatigues.

For a circuit of multiple capacitors, calculating the equivalent capacitance requires separate equations. Equation 2 is derived for capacitors in parallel, and Equation 2 is for capacitors in series. In these equations, the variables $C_1$, $C_2$, and $C_3$ are all constructed with the same dielectric material, where $C_n$ is the $n^{th}$ capacitor.

$$C_{parallel} = C_1 + C_2 + \ldots + C_n \qquad \text{Equation 2.}$$

$$C_{series} = \frac{1}{\frac{1}{C_1} + \frac{1}{C_2} + \ldots + \frac{1}{C_n}}. \qquad \text{Equation 3}$$

Changes in the dielectric constant (K) can occur as a result of degradation of the layers over time. For example, during investigations leading to the present invention, certain rubber materials which initially had relatively high dielectric constant values were found to experience a decrease in dielectric constant values with prolonged exposure to heat. In view of Equation 1, as dielectric constant decreases, capacitance also decreases in a linear relationship. Therefore, if the initial dielectric constant value of the innermost conductive layer (38 or 46) is known, the degradation of the innermost conductive layer (38 or 46) may be measured over time using capacitance measurements.

If the first conductive layer 38 fails, pressure within the hose will likely force fluid to penetrate between the first conductive layer 38 and the first dielectric layer 32. Under these conditions, the dielectric constant value would be a proportional combination of the dielectric constant values of the fluid and the first dielectric layer 32. Since the dielectric constant and capacitance share a linear relationship as mentioned previously and most hydraulic fluids generally have a very low dielectric constant value, a breach in the first conductive layer 38 will likely result in a substantial decrease in measured capacitance.

Most hose failures will likely occur with changes to both the value of the dielectric constant and the thickness of the layers. For example, as the first conductive layer 38 begins to weaken over time, the pressure from the fluid may thin areas of the layer. Due to the relationship between the thickness of the layers and capacitance, it is possible that a failure in the innermost layers of the hose may result in a decrease or an increase in the measured capacitance. For example, spiral wire failures may cause expansion and contraction of layers within a hose causing compression of the dielectric layers and a subsequent change in capacitance. Consequently, it is believed that a relatively simple method of monitoring a hose is to identify and specify failure limits or thresholds both above and below the initial capacitance measurements of an undamaged hose. This will promote the system's ability to predict failure of the hose regardless of the specific mode of failure that may occur.

In view of the above, it can be seen that a significant advantage of this invention is that methods and devices are provided that are particularly well suited for sensing and predicting failure in high pressure hoses.

While the invention has been described in terms of specific embodiments, it is apparent that other forms could be adopted by one skilled in the art. For example, the physical configuration of the hoses and fittings could differ from that shown, and materials and processes/methods other than those noted could be used. Therefore, the scope of the invention is to be limited only by the following claims.

The invention claimed is:

1. A system for predicting structural failure of at least a portion of a wall of a high pressure hydraulic hose, the wall having an innermost layer for contact with a fluid contained by the hose, an outermost layer parallel with the innermost layer, and at least one reinforcement layer that comprises a spiral metal wire and is between the innermost and outermost layers and parallel to the innermost layer, the system comprising:
    strain-sensing means within the portion of the wall and surrounded by the at least one reinforcement layer, the strain-sensing means comprising at least one conductor that is parallel to the outermost layer of the wall and at the innermost layer of the wall;
    a fitting secured to the hose and having a nipple that is within an opening of the innermost layer of the hose and in direct electrical contact with the at least one conductor; and
    means for sensing changes in an electrical property associated with the at least one conductor resulting from distortion of the wall of the hose causing distortion of the at least one conductor, the sensing means comprising an electrical connection through the direct electrical contact between the nipple and the at least one conductor, the electrical property being chosen from the group consisting of electrical capacitance, electrical resistance, electrical inductance, electrical reactance, and combinations thereof.

2. The system of claim 1, further comprising:
    means for establishing an acceptable range for the electrical property; and
    means for generating a signal that a structural failure of the innermost layer is impending or has occurred in response to the electrical property deviating outside the acceptable range.

3. The system of claim 1, wherein the hose further comprises:
    a dielectric layer in contact with the inner conductive layer and parallel to the outermost layer; and
    a outer conductive layer in contact with the dielectric layer and parallel to the outermost layer.

4. The system of claim 3, wherein the at least one outer conductive layer is a metallic reinforcement layer surrounded by the at least one reinforcement layer.

5. The system of claim 3, wherein the inner and outer conductive layers are formed of materials chosen from the group consisting of metal, conductive polymer, and conductive fiber materials.

6. The system of claim 3, wherein the dielectric layer is formed of materials chosen from the group consisting of dielectric polymer and dielectric fiber materials.

7. The system of claim 1, wherein the hose comprises:
    at least two capacitance bridges each defined by an inner conductive layer, an outer conductive layer, and a dielectric layer therebetween.

8. The system of claim 1, wherein the hose comprises a plurality of alternating conductive layers and dielectric layers.

9. A method of predicting structural failure of at least a portion of a wall of a high pressure hydraulic hose containing a fluid, the method comprising the steps of:

forming the wall to have an innermost layer for contact with a fluid contained by the hose, an outermost layer parallel with the innermost layer, at least one reinforcement layer that comprises a spiral metal wire and is between the innermost and outermost layers and parallel to the innermost layer, and strain-sensing means within the portion of the wall and surrounded by the at least one reinforcement layer, the strain-sensing means comprising at least one conductor that is parallel to the outermost layer of the wall and at the innermost layer of the wall;

securing a fitting to the hose so that a nipple is within an opening of the innermost layer of the hose and in direct electrical contact with the at least one conductor; and sensing changes in an electrical property associated with the at least one conductor resulting from distortion of the wall of the hose causing distortion of the at least one conductor, the sensing step comprising an electrical connection through the direct electrical contact between the nipple and the at least one conductor, the electrical property being chosen from the group consisting of electrical capacitance, electrical resistance, electrical inductance, electrical reactance, and combinations thereof.

10. The method of claim 9, further comprising:
establishing an acceptable range for the electrical property; and
generating a signal that a structural failure of the wall is impending in response to the electrical property deviating outside the acceptable range.

11. The method of claim 9, wherein the strain-sensing means is formed to further comprise:
a dielectric layer parallel to and contacting the inner conductive layer; and
an outer conductive layer parallel to and contacting the dielectric layer.

12. The method of claim 11, wherein the outer conductive layer is formed as a metallic reinforcement layer surrounded by the at least one reinforcement layer.

13. The method of claim 9, wherein the strain-sensing means is formed to comprise at least two capacitance bridges each defined by an inner conductive layer, an outer conductive layer, and a dielectric layer therebetween and in contact with the inner conductive layer and the outer conductive layer, wherein the inner conductive layer, the outer conductive layer, and the dielectric layer are parallel to the outermost layer.

14. The method of claim 9, wherein the strain-sensing means is formed to comprise a plurality of alternating conductive layers and dielectric layers.

* * * * *